United States Patent [19]

Koyfman et al.

[11] Patent Number: 5,275,618
[45] Date of Patent: Jan. 4, 1994

[54] JET ENTANGLED SUTURE YARN AND METHOD FOR MAKING SAME
[75] Inventors: Ilya Koyfman, Orange; Michael P. Chesterfield, Norwalk, both of Conn.
[73] Assignee: United States Surgical Corporation, Norwalk, Conn.
[21] Appl. No.: 791,422
[22] Filed: Nov. 13, 1991
[51] Int. Cl.⁵ .............................................. A61B 17/00
[52] U.S. Cl. .............................. 606/228; 57/308; 57/350; 57/908; 28/274
[58] Field of Search .................................. 28/271–; 57/308, 350, 284, 290, 274, 206, 255; 606/228–

[56] References Cited

U.S. PATENT DOCUMENTS

| | | |
|---|---|---|
| 2,985,395 | 5/1961 | Bunting, Jr. et al. . |
| 3,069,836 | 12/1962 | Dahlstrom et al. . |
| 3,115,691 | 12/1963 | Bunting, Jr. et al. . |
| 3,125,095 | 3/1964 | Kaufman et al. . |
| 3,187,752 | 6/1965 | Glick ................................ 606/231 |
| 3,238,590 | 3/1966 | Nicita et al. . |
| 3,262,179 | 7/1966 | Sparling . |
| 3,286,321 | 11/1966 | Fletcher et al. . |
| 3,329,757 | 7/1967 | Johnson . |
| 3,359,983 | 12/1967 | Northey . |
| 3,439,491 | 4/1969 | Scruggs ................................ 57/160 |
| 3,443,451 | 5/1969 | Zieber, Jr. . |
| 3,501,819 | 3/1970 | Satterwhite ........................ 57/245 |
| 3,568,426 | 3/1971 | Whitley ................................ 57/206 |
| 3,751,775 | 8/1973 | Psaras . |
| 3,780,515 | 12/1973 | Waters . |
| 3,791,388 | 2/1974 | Hunter et al. .................... 606/229 |
| 3,828,404 | 8/1974 | Peckinpaugh et al. . |
| 3,889,327 | 6/1975 | Joly et al. . |
| 3,949,755 | 4/1976 | Vauquois ........................... 606/229 |
| 3,994,121 | 11/1976 | Adams . |
| 4,005,566 | 2/1977 | Hawkins . |
| 4,051,660 | 10/1977 | Griset, Jr. . |
| 4,055,039 | 10/1977 | Movshovich et al. . |
| 4,080,778 | 3/1978 | Adams et al. . |
| 4,100,725 | 7/1978 | Magel ................................ 57/255 |
| 4,118,921 | 10/1978 | Adams et al. . |
| 4,251,904 | 2/1981 | Sano et al. ......................... 28/274 |
| 4,321,038 | 3/1982 | Porteous . |
| 4,351,146 | 9/1982 | Faure et al. . |
| 4,384,018 | 5/1983 | Caswell et al. . |
| 4,414,800 | 11/1983 | Nakayama et al. ................ 57/236 |
| 4,430,853 | 2/1984 | Scott et al. ........................ 57/247 |
| 4,484,436 | 11/1984 | Nakayama et al. ................ 57/328 |
| 4,505,013 | 3/1985 | Nelson ................................ 28/274 |
| 4,546,769 | 10/1985 | Planck et al. .................... 606/228 |
| 4,563,799 | 1/1986 | Dammann ........................... 28/274 |
| 4,570,312 | 2/1986 | Whitener, Jr. ..................... 28/274 |
| 4,610,131 | 9/1986 | Eschenbach et al. ............. 57/6 |
| 4,615,167 | 10/1986 | Greenberg ......................... 28/220 |
| 4,639,986 | 2/1987 | Borenstein ......................... 28/274 |
| 4,644,622 | 2/1987 | Bauer et al. ...................... 28/274 |
| 4,662,886 | 5/1987 | Moorse et al. .................... 623/13 |
| 4,666,395 | 5/1987 | Shah .................................. 425/377 |
| 4,685,179 | 8/1987 | Sheehan et al. .................. 28/248 |
| 4,715,097 | 12/1987 | Bogucki-Land .................... 28/274 |
| 4,719,576 | 1/1988 | Sano et al. . |
| 4,719,837 | 1/1988 | McConnell et al. . |
| 4,754,527 | 7/1988 | Gilhaus .............................. 28/274 |
| 4,779,408 | 10/1988 | Nelson ................................ 57/284 |
| 4,792,336 | 12/1988 | Hlavacek et al. ................. 623/13 |
| 4,878,280 | 11/1989 | Nelson et al. ..................... 28/274 |
| 4,942,875 | 7/1990 | Hlavacek et al. ................. 606/230 |
| 4,946,467 | 8/1990 | Ohi et al. .......................... 606/228 |
| 4,949,441 | 8/1990 | Ethridge ............................. 28/271 |
| 4,959,069 | 9/1990 | Brennan et al. .................. 606/228 |
| 4,974,488 | 12/1990 | Karhu . |
| 5,012,636 | 5/1991 | Hallam et al. .................... 57/204 |
| 5,019,093 | 5/1991 | Kaplan et al. .................... 606/228 |

OTHER PUBLICATIONS

Fibreguide Brochure, Fibreguide Ltd. Maple Court, Davenport Street, Macclesfield, Cheshire SK10 1JE, England.

*Primary Examiner*—Stephen C. Pellegrino
*Assistant Examiner*—Gary Jackson
*Attorney, Agent, or Firm*—Thomas R. Bremer; Peter G. Dilworth; Rocco S. Barrese

[57] ABSTRACT

A method for making a multifilament suture yarn includes jet entangling the filaments of the suture yarn prior to other operations such as twisting and braiding. A multifilament braided suture is made of air entangled suture yarns, such as by braiding. The suture may include a core constructed of entangled yarns, preferably in the form of a cabled core constructed of multiple entangled yarns plied together, the plied yarns being air entangled and twisted in a first direction. Multiple entangled plied yarns twisted in the first direction are combined and twisted in a second opposite direction to form a cabled core.

23 Claims, 1 Drawing Sheet

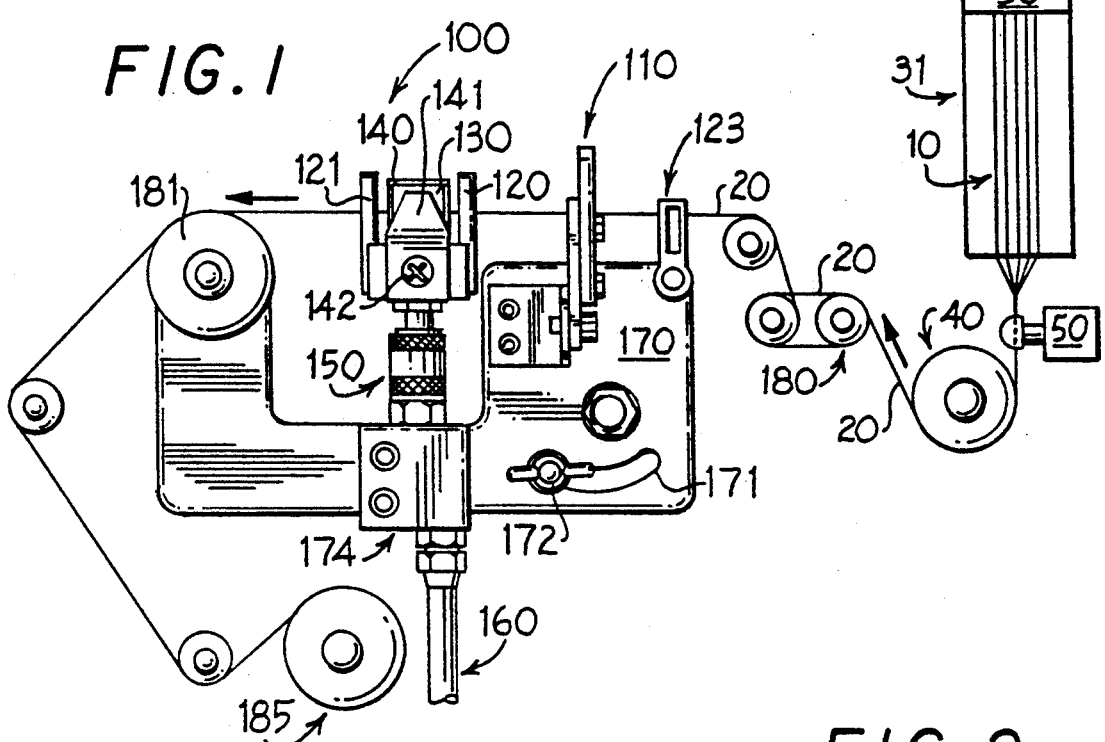
FIG. 1
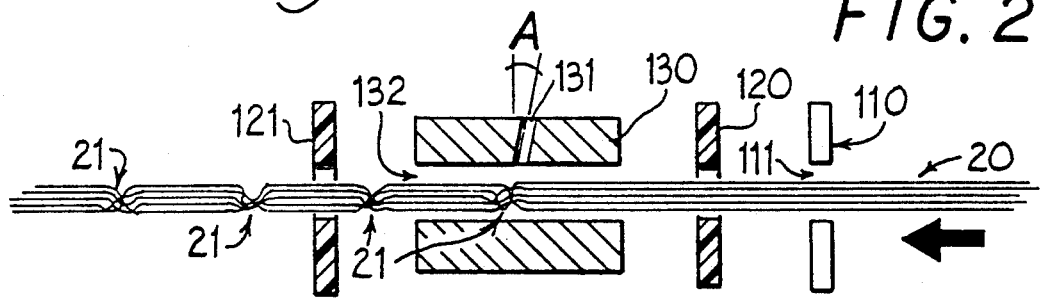
FIG. 2
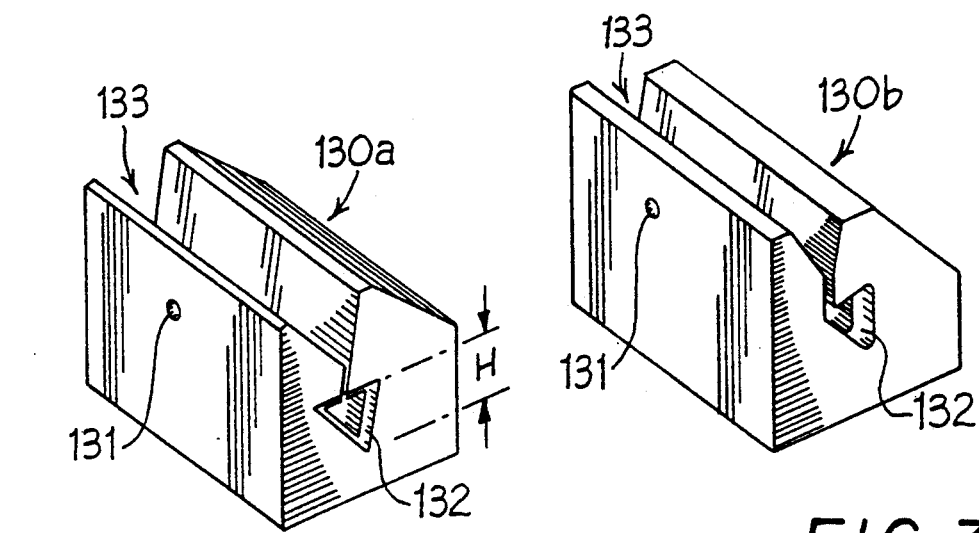
FIG. 3A
FIG. 3B

JET ENTANGLED SUTURE YARN AND METHOD FOR MAKING SAME

BACKGROUND OF THE INVENTION

1. Field of the Invention

The present invention relates to multifilament suture yarn and to a method for making same.

2. Background of the Art

Sutures intended for the repair of body tissues must meet certain requirements: they must be substantially non-toxic, capable of being readily sterilized, they must have good tensile strength and have acceptable knot-tying and knot-holding characteristics and if the sutures are of the absorbable or biodegradable variety, the absorption or biodegradation of the suture must be closely controlled.

Sutures have been constructed from a wide variety of materials including surgical gut, silk, cotton, a polyolefin such as polypropylene, polyamide, polyglycolic acid, polyesters such as polyethylene terephthalate and glycolide-lactide copolymer, etc. Although the optimum structure of a suture is that of a monofilament, since certain materials of construction would provide a stiff monofilament suture lacking acceptable knot-tying and knot-holding properties, sutures manufactured from such materials are preferably provided as braided structures. Thus, for example, sutures manufactured from silk, polyamide, polyester and bio-absorbable glycolide-lactide copolymer are usually provided as multifilament braids. Commercial examples of such sutures include DEXON (David & Geck, Inc.) and VICRYL (Ethicon, Inc.).

Typically, braided sutures comprise an arrangement of discrete units, or bundles, denominated "sheath yarns", each sheath yarn being made up of individual filaments with the sheath yarns interlacing in a regular criss-cross pattern.

Optionally a core component may be included. The core may be a cabled structure made up of plied yarns each of which has been given a twist in one direction, the plied yarns then being combined to form a core which is then given a twist in a second, opposite direction.

As spun or zero twist yarn consists of filaments which are essentially parallel to each other and which are held in contiguity by a treating fluid, i.e., spin finish, which includes lubricants and other agents to facilitate processing of the yarn. As spun yarn is subject to defects which impair handling and processing characteristics of the yarn and the finished suture. For example, filaments can snag and break during processing, thereby causing defects such as fluff balls, slubs, and ringers. The surface characteristics of the finished suture are very important and must research and development has been performed in the suture field to improve the surface characteristics, especially the surface smoothness, of multifilament sutures. Surface defects caused by broken filaments add to the roughness of the suture and increases the "drag" or "chatter" of the suture at it is drawn through body tissue. Trauma to tissue is increased as a rough suture is pulled through tissue. Such defects, therefore, militate against smooth, neat, accurately placed wound approximation so necessary to excellence in surgical practice.

One way of reducing the defects mentioned above is to twist the individual filaments. Twisting compacts and unifies the yarn thereby resulting in a more cohesive structure. However, twisting greatly increases the processing costs. Moreover, as the yarn is subjected to an extra step of mechanical handling, it is more subject to be damaged. The fewer operations the filaments are subjected to during processing the less chance there is of breakage.

Another consideration is the denier of the individual filaments. From the standpoint of surface characteristics lower denier filaments are preferable for reducing the surface roughness and the attendant drag and chatter as the suture is drawn through body tissue. However, smaller denier filaments break more easily than larger denier filaments in certain processing.

What is needed, then, is a method which allows the manufacture of suture yarn without the twisting operation and having as few or fewer defects per length of suture as compared with currently used methods.

SUMMARY OF THE INVENTION

A method for making a surgical suture is provided herein. The method comprises: providing a plurality of filaments of surgical suture material; combining the filaments into a yarn; and passing the yarn through a fluid jet intermingling zone which includes an enclosed passageway, impinging at least one jet of fluid such as air under fluid pressure higher than ambient pressure upon said yarn to intermingle the filaments thereof, thereby forming an entangled yarn. The suture material can be a synthetic polymer and can be bioabsorbable or non-bioabsorbable.

The fluid jet pulsates so as to form discrete spaced apart regions of entanglement along the length of the suture yarn.

Further contemplated as part of the invention is combining a length of the entangled yarn with a length of at least one other entangled yarn to form a plied suture core yarn; entangling the suture core yarn in accordance with the entanglement method mentioned above, and twisting the entangled core yarn; then combining a length of the twisted and entangled core yarn with a length of at least one other twisted and entangled core yarn, each entangled core yarn having been twisted in the same direction; and then twisting said combined twisted and entangled core yarns in the opposite direction to form a suture core.

The suture also includes a braided sheath formed by combining a length of entangled yarn with a length of at least one other entangled yarn to form a suture sheath yarn; entangling the suture sheath yarn in accordance with the entanglement method mentioned above; and, braiding said entangled sheath yarn with from about 3 to about 35 other entangled sheath yarns around said suture core to form a finished braided suture. Optionally, the suture can be formed from a braided sheath yarn without a core. Air entangling the suture yarns eliminates any need to twist the sheath yarns, thereby advantageously reducing in process handling of the yarns and reducing equipment and processing costs.

Usually an amount of spin finish is applied to the individual filaments prior to combining said filaments into a yarn, and then substantially all of the spin finish is removed from the finished suture. The amount of spin finish applied to said filaments is about 50% less than the amount of spin finish required without employing the entanglement step. Because spin finish must be removed in a subsequent washing steps, reduced spin finish advantageously facilitates processing.

BRIEF DESCRIPTION OF THE DRAWINGS

FIG. 1 is a diagrammatic illustration of the method and apparatus used in the present invention.

FIG. 2 is a sectional plan view of the jet entanglement apparatus.

FIG. 3a is a perspective view of a body element useful in the entanglement apparatus.

FIG. 3b is a perspective view of an alternative body element useful in the jet entanglement apparatus.

DETAILED DESCRIPTION OF PREFERRED EMBODIMENT(S)

The filaments included in the suture of the present invention may be fabricated from non-bioabsorbable materials such as silk, cotton, polypropylene, polyolefins, polyamide, polyethylene, polyethylene terephthalate, etc.

In a preferred embodiment, the suture of the present invention is fabricated from filaments extruded from a bio-absorbable or biodegradable resin such as one derived from polyglycolic acid, glycolide, lactic acid, lactide, dioxanone, trimethylene carbonate, etc., and various combinations of these and related monomers. Sutures prepared from resins of this type are known in the art, e.g., as disclosed in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,060,089; 4,137,921; 4,157,437; 4,234,775; 4,237,920; 4,300,565; and 4,523,591; U.K. Patent No. 779,291; D.K. Gilding et al., "Biodegradable polymers for use in surgery—polyglycolic/poly(lactic acid) homo- and copolymers: 1, Polymer, Volume 20, pages 1459–1464 (1979), and D. F. Williams (ed.), Biocompatibility of Clinical Implant Materials, Vol. II, ch. 9: "Biodegradable Polymers" (1981).

The suture construction method of the present invention includes the following initial steps:
1. Providing individual filaments
2. Combining the filaments to form a yarn
3. Jet Entanglement of the yarn These steps are illustrated in FIG. 1 which is a diagrammatic illustration thereof.

1. Providing Individual Filaments

Wherein the suture is fabricated from a polymeric resin, the individual filaments are optimally prepared by extrusion from a polymer melt. Extrusion processes are well known in the art. FIG. 1 digrammatically illustrates as spun filaments 10 extruded through spinneret 30 and quenched in chamber 31.

For sheath or core construction the filaments can have a denier ranging from about 0.2 to 6 denier, preferably about 0.8 to about 3.0 denier, and more preferably 0.8 to 1.8 denier, depending on the overall suture denier. Low denier is especially desirable in sheath filaments to maintain smooth surface characteristics, whereas core filaments may optionally have a higher denier, especially for sutures with a high overall denier.

2. Combining filaments to form a yarn

The number of filaments present in a yarn will depend on the overall denier of the suture and whether the yarn is to be incorporated into a sheath or core. Table I below sets forth typical numbers of filaments per yarn.

TABLE I

| | NUMBER OF FILAMENTS PER YARN |
| --- | --- |
| FILAMENT DENIER | APPROXIMATE RANGE OF FILAMENT NUMBER PER YARN |
| 0.2 | 45 to 450 |
| 0.5 | 15 to 150 |
| 1.5 | 5 to 50 |
| 1.8 | 3 to 40 |
| 6.0 | 1 to 15 |

After the as spun filaments 10 are quenched, a spin finish applicator 50 applies spin finish to the filaments which are then passed around lube godet 40. During this procedure, the filaments 10 combine in parallel contiguous arrangement to form yarn 20. Yarn 20 is then passed around a series of godets 180 for drawing and relaxing the suture yarn. The yarn speed can be from about 200 to about 1000 meters per minute, preferably about 600 to about 800 meters per minute, and more preferably about 700 to about 800 meters per minute. The yarn is under a tension of from about 3 to about 10 grams, preferably about 3 to about 7 grams, and more preferably from about 3 to about 5 grams.

3. Jet Entanglement

The yarn 20 from step 2 above is sent to a jet entanglement apparatus 100.

In jet entanglement a fluid, preferably air or some other gas, is forced at elevated pressure into a chamber through which a multifilament yarn is passed. The turbulence of the jet causes the filaments to entangle or intermingle in the area impinged by the jet. The movement of the yarn and the size and shape of the chamber can interact to cause pulsations in the turbulence. Thus, even with a constant pressure air supply, the yarn can exit the chamber with discrete regularly spaced apart areas of entanglement alternating with non-entangled areas. The entangled portions are retained by the yarn through subsequent processing steps. Jet entanglement can accomplish many of the features of twisting with a simpler and less costly method.

Referring to FIGS. 2, 3a, and 3b in conjunction with FIG. 1, jet entangler apparatus 100 comprises slub catcher 110, eyelets 123, 120 and 121, support frame 140, quick release adjustment 150, air supply line 160, mounting plate 170 for supporting the apparatus which includes adjustment slot 171 with adjustment wing nut 172, support block 174, roller 181, and body element 130.

An apparatus suitable for use in the present invention is available from Fiberguide Ltd., located at Maple Court, Davenport Street, Macclesfield, Cheshire SK10 1 JE, England. Especially suitable are Models FG-1 and FG-4.

The body element 130 is preferably fabricated as an integral single piece from a hard, durable material such as tungsten carbide, ceramic coated steel, or solid ceramic. Body element 130 possesses a chamber 132 extending lengthwise along the moving path of the threadline in which the entanglement takes place. A threading slot 133 facilitates easy threading of the suture yarn within the chamber. The chamber is preferably of triangular cross section to facilitate turbulence. The height H of the chamber 132, i.e., the distance from the base to the apex of the triangle, can be from about 2.0 millimeters to about 5 millimeters, more preferably from about 2.3 millimeters to about 4.3 millimeters. Air, or other suitable gas, is introduced into the chamber 130 via orifice 131, which may be oriented at angle A from a line perpendicular to the longitudinal path of the threadline. Angle A can be from about 0° to about 15°. The air is introduced to the chamber 130 at a pressure of from about 10 to 100 psi, preferably 30 to 90 psi, and more preferably 60 to 80 psi.

The diameter of orifice 131 can range from about 1 to 3 millimeters, and more preferably from about 1 to 1.5 millimeters.

The body element 130 is secured to the support frame 140 by means of locking plate 141 and locking screw 142. Quick release connection 150 which is secured to support block 174 and which, in turn, supports body element support frame 140, allows for consistent and precise positioning of the body element 13 between eyelets 120 and 121.

The body element can be of any of the various configurations and dimensions suitable for the suture entanglement process of the present invention. FIG. 3A illustrates a body element 130a such as from the FG-1 model entangler from Fiberguide. The triangular shaped chamber 132 is oriented with apex pointing downward. The height H of the chamber 132 can be from 2.3 to about 4.1 mm. A preferred size for the channel for a yarn having a denier of about 10 to about 100 is about 2.3 mm in conjunction with an orifice diameter of about 1.3 mm.

FIG. 3B illustrates a body element 130b of the FG-4 model entangler from Fiberguide. The triangular shaped chamber 132 is oriented with its apex pointing sideways.

Referring again to FIGS. 1 and 2, after suture yarn 20 is passed over godets 180, it is then passed through eyelet 123, and through slot 111 in slub catcher 110, and through eyelet 120 and into chamber 130 at a preferred speed of about 750 meters per minute. Air is ejected from orifice 130 at preferably about 70 psi and preferably at an angle A of about 5°. The turbulence is characterized by pulsations, i.e., discrete impingements of air upon the suture yarn, which produce from about 20 to 80 impingements 21 or regions of entanglement per meter of suture yarn length, i.e., an impingement spacing of 12.5 mm to about 50 mm. A preferred range is 35 to 50 impingement per meter, (i.e., an impingement spacing of 20 mm to about 29 mm).

After exiting from chamber 132, entangled yarn 20 passes through eyelet 121 around roller 181, and onto a take up spool 185.

4. Subsequent Processing

The entangled yarn 20 may be combined with other entangled yarns and further entangled in conjunction with twisting or braiding operations. Sutures can optionally be provided with yarns comprising a separately constructed core around which sheath yarns are braided. In a preferred embodiment 3 to 7 entangled yarns from step 3 above are further combined and entangled to form a plied entangled yarn which is then twisted. The plied yarn is then combined with other plied yarns, each yarn having been twisted in the same direction. The combined plied yarns are then combined and twisted in the opposite direction to form a cabled core unit around which the remainder of the suture is constructed. The degree of twist which is applied to the yarns can vary widely with from about 200 to about 1500 turns per meter, and preferably from about 240 to about 1200 turns per meter generally providing good results. Alternatively, it is contemplated that the need to ply multiple yarns can be eliminated by spinning large denier yarns having hundreds of filaments. The large denier yarns, on the order of from about 100 to about 1000 denier, are jet entangled in accordance with the invention and multiple twisted large denier yarns are combined and twisted in the opposite direction to form a cabled core.

Sheath yarns do not need to be plied. From about 4 to about 36 sheath yarns may be braided around the aforementioned core to form the finished suture. Alternatively, the finished suture may be braided with sheath yarns only, and without a core.

More information about the preferred braided sutures may be found in U.S. Pat. No. 5,019,093, herein incorporated by reference. More information about the preferred cabled core structures can be found in U.S. application Ser. No. 07/733,362 filed Jul. 19, 1991.

It is also within the scope of this invention to impregnate the suture with, or otherwise apply thereto, one or more medico-surgically useful substances, e.g.; those which accelerate or beneficially modify the healing process when the suture is applied to a wound or surgical site. So, for example, the braided suture herein can be provided with a therapeutic agent which will be deposited at the sutured site. The therapeutic agent can be chosen for its antimicrobial properties, capability for promoting wound repair and/or tissue growth or for specific indications such as thrombosis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a surgical or trauma wound site. To promote wound repair and/or tissue growth, one or several growth promoting factors can be introduced into the suture, e.g., fibroblast growth factor, bone growth factor, epidermal growth factor, platelet derived growth factor, macrophage derived grown factor, alveolar derived growth factor, monocyte derived growth factor, magainin, and so forth. Some therapeutic indications are: glycerol with tissue or kidney plasminogen activator to cause thrombosis, superoxide dismutase to scavenge tissue damaging free radicals, tumor necrosis factor for cancer therapy or colony stimulating factor and interferon, interleukin-2 or other lymphokine to enhance the immune system.

Further information regarding appropriate suture filling materials, including medico-useful substances, may be found in U.S. Pat. Nos. 5,037,429, and 5,051,272 both of which are hereby incorporated by reference herein.

5. Advantages

The jet entanglement process offers several surprising advantages with respect to surgical suture fabrication. First, the required amount of spin finish is reduced. Spin finish is a fluid applied to the filaments after extrusion to improve processability. Spin finish includes such agents as lubricants and antistatic agents. After processing, however, the spin finish must be removed by washing before the suture is packaged. Hence, a reduction in the required amount of spin finish would provide advantageous cost reduction at two stages of operation: the application of the spin finish and its removal. Surprisingly, when air entanglement is employed the amount of spin finish required for processing is reduced by about 50%. Thus, considerable savings are realized.

Jet entanglement obviates the need for a twisting operation. Thus, considerable savings in terms of the capital cost of twisting equipment, facilities, and other related costs are realized.

Another advantage of the present invention is that yarn processability is improved and breakage of filaments is reduced. Even if a filament breaks it can only strip back as far as the next closest impingement or entanglement area, which is generally no more than about 12 to 50 mm distance. In addition, air entanglement advantageously tends to imbed broken ends of filaments within the suture yarn, reducing the likelihood that the broken filaments will accumulate during further processing. These results are especially important when the individual filaments possess a low denier, i.e., a denier less than about 2. Hence, yet another advantage of employing jet entanglement is that it enables the suture to be made from filaments of low denier at a low defect rate. As mentioned above, use of lower denier filaments is desired because lower denier filaments result in a smoother suture.

The results of the air entanglement process of the present invention depends on the balancing of several variables: air pressure, yarn tension, orifice size, impingement angle, spin finish level, and chamber dimensions. These variables may be adjusted in accordance with the desired results for any particular type of yarn. While the above description contains many specifics, these specifics should not be construed as limitations on the scope of the invention, but merely as ememplifications of preferred embodiments thereof. Those skilled in the art will envision many other possible variations that are within the scope and spirit of the invention as defined by the claims appended hereto.

What is claimed is:

1. A method for making a surgical suture, comprising:
   a) providing a plurality of filaments of surgical suture material;
   b) combining said filaments into a yarn; and,
   c) passing said yarn through a fluid jet intermingling zone which includes an enclosed passageway with a yarn entrance and yarn exit, and in said passageway, impinging at least one jet of fluid under fluid pressure higher than ambient pressure upon said yarn to intermingle the filaments thereof, thereby forming an entangled yarn;
   d) combining a length of the entangled yarn with a length of at least one other entangled yarn to form a surgical suture.

2. The method of claim 1, wherein said surgical suture material is a synthetic polymer.

3. The method of claim 1, wherein said surgical suture material is bioabsorbable.

4. The method of claim 3, wherein said bioabsorbable suture material is selected from the group consisting of polymers of glycolide, lactide, caprolactone, p-dioxanone, and physical and chemical combinations thereof.

5. The method of claim 1, wherein said fluid is air.

6. The method of claim 1, wherein said fluid pressure is from about 10 to 100 psi.

7. The method of claim 1, wherein said fluid pressure is from about 30 to 90 psi.

8. The method of claim 1, wherein said fluid pressure is from about 60 to 80 psi.

9. The method of claim 1, wherein said passageway possesses a generally triangular shaped cross-section.

10. The method of claim 1, wherein said fluid jet is directed from an orifice having an opening in the passageway, said orifice being oriented at an angle of from about 0° to about 15° from a line perpendicular to the longitudinal path of the yarn.

11. The method of claim 10, wherein said orifice has a diameter of from about 1 to 1.5 millimeters.

12. The method of claim 1, wherein said fluid jet is pulsating so as to form discrete spaced apart regions of entanglement along the length of the suture yarn.

13. The method of claim 1, wherein said yarn is passed through said passageway with a speed of from about 200 to about 1000 meters per minute.

14. The method of claim 1, wherein said yarn is passed through said passageway at a speed of from about 600 to 800 meters per minute.

15. The method of claim 1, wherein the denier of the individual filaments is from about 0.2 to about 6.0.

16. The suture of claim 1, wherein the denier of the individual filaments is from about 0.8 to about 3.0.

17. The suture of claim 1, wherein the denier of the individual filaments is from about 0.8 to about 1.8.

18. The method of claim 1, further comprising:
braiding a length of entangled yarn from step (c) with from about 3 to about 35 other entangled yarns to form a finished braided suture.

19. The method of claim 18, further comprising adding a medically effective amount of a therapeutic agent to said finished braided suture.

20. The method of claim 1, wherein said entagled yarns are combined by braiding.

21. A method for making a surgical suture yarn comprising:
   a) providing a plurality of filaments of surgical suture material;
   b) combining said filaments into a yarn;
   c) passing said yarn through a fluid jet intermingling zone which includes an enclosed passageway with a yarn entrance and a yarn exit, and in said passageway, impinging at least one jet of fluid under fluid pressure higher than ambient pressure upon said yarn to intermingle the filaments thereof, thereby forming an entangled yarn;
   d) combining a length of entangled yarn with a length of at least one other entangled yarn to form a plied yarn;
   e) entangling the plied yarn in accordance with the method of step (c);
   f) twisting said plied yarn;
   g) combining a length of said twisted plied yarn with a length of at least one other twisted plied yarn, each plied yarn having been twisted in the same direction; and,
   h) twisting said combined plied yarns in the opposite direction to form a suture core.

22. The method of claim 21, further comprising:
braiding a length of entangled yarn from step (c) with from about 3 to about 35 other entangled yarns around said suture core to form a finished braided suture.

23. The method of claim 22, further comprising adding a medically effective amount of a therapeutic agent to said finished braided suture.

* * * * *